US009828584B2

(12) United States Patent
Baek et al.

(10) Patent No.: US 9,828,584 B2
(45) Date of Patent: Nov. 28, 2017

(54) METHOD FOR INDUCING HEMOBLAST DIFFERENTIATION

(71) Applicant: INDUSTRY-UNIVERSITY COOPERATION FOUNDATION HANYANG UNIVERSITY, Seoul (KR)

(72) Inventors: Eun Jung Baek, Seoul (KR); Eun Mi Lee, Gyeonggi-do (KR)

(73) Assignee: INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 312 days.

(21) Appl. No.: 14/427,700

(22) PCT Filed: Sep. 11, 2013

(86) PCT No.: PCT/KR2013/008226
§ 371 (c)(1),
(2) Date: Sep. 8, 2015

(87) PCT Pub. No.: WO2014/042432
PCT Pub. Date: Mar. 20, 2014

(65) Prior Publication Data
US 2016/0060600 A1    Mar. 3, 2016

(30) Foreign Application Priority Data
Sep. 12, 2012 (KR) .................. 10-2012-0100821

(51) Int. Cl.
| | | |
|---|---|---|
| *A61K 38/17* | (2006.01) | |
| *C12N 5/078* | (2010.01) | |
| *C12N 5/0787* | (2010.01) | |
| *A61K 35/15* | (2015.01) | |
| *A61K 35/18* | (2015.01) | |

(52) U.S. Cl.
CPC ............ *C12N 5/0641* (2013.01); *A61K 35/15* (2013.01); *A61K 35/18* (2013.01); *A61K 38/1709* (2013.01); *C12N 5/0642* (2013.01); *C12N 2500/99* (2013.01); *C12N 2501/125* (2013.01); *C12N 2501/14* (2013.01); *C12N 2501/2303* (2013.01); *C12N 2501/48* (2013.01); *C12N 2501/998* (2013.01); *C12N 2506/025* (2013.01); *C12N 2506/11* (2013.01)

(58) Field of Classification Search
CPC ............ C12N 5/0641; C12N 5/0642; C12N 2501/998; C12N 2506/11; A61K 38/1722; A61K 38/1709
See application file for complete search history.

(56) References Cited

U.S. PATENT DOCUMENTS

| | | | | |
|---|---|---|---|---|
| 5,691,160 | A * | 11/1997 | Janmey .............. | A61K 38/1709 435/13 |
| 7,935,348 | B2 * | 5/2011 | Mattner ................ | A61K 38/08 424/140.1 |
| 9,316,639 | B2 * | 4/2016 | Stossel ................ | G01N 33/564 |
| 9,408,891 | B2 * | 8/2016 | Janmey .............. | A61K 38/1709 |
| 2007/0238668 | A1 | 10/2007 | Janmey et al. ................ | 514/15 |

FOREIGN PATENT DOCUMENTS

| | | |
|---|---|---|
| KR | 10-2005-0008757 A | 1/2005 |
| KR | 10-2010-0081678 A | 7/2010 |
| KR | 10-2012-0003760 A | 1/2012 |
| WO | WO 2007/106577 | 9/2007 |

OTHER PUBLICATIONS

Cantu et al., Haematologica. Jul. 2012;97(7):980-988.*
International Search Report for peT IKR2013/008226.
Giarratana, M-C., et al., (2005). "Ex vivo generation of fully mature human red blood cells from hematopoietic stem cells", *Nature Biotechnology, Nature Publishing Group*, US, 23(1):69-74.
Hinssen, H., et al., (1987). "Gelsolin is expressed in early erythroid progenitor cells and negatively regulated during erythropoiesis", *The Journal of Cell Biology*, 105:1425-1433.
Peng, K-W., et al., (2012). "Differential role of actin-binding proteins in controlling the adipogenic differentiation of human CD105-positive wharton's jelly cells", *Biochimica et Biophysica Acta (bba)—General Subjects*, 1820(4):469-481.
Shirkoohi, R., et al., (2012). "Gelsolin induces promonocytic leukemia differentiation accompanied by upregulation of p21CIP1", *Asian Pacific J Cancer Prev*, 13(9):4827-4834.

* cited by examiner

*Primary Examiner* — Daniel C Gamett
(74) *Attorney, Agent, or Firm* — Harness, Dickey & Pierce, P.L.C.

(57) ABSTRACT

The present invention relates to the in vitro production of erythrocytes/granulocytes and to the treatment of myelodysplastic syndrome using a method for inducing hemoblast differentiation. The present invention provides a media composition comprising gelsolin as an active ingredient for inducing the differentiation of hematopoietic precursor cells into erythrocytes/granulocytes, and a pharmaceutical composition comprising gelsolin as an active ingredient for treating myelodysplastic syndrome. Since the composition of the present invention improves the efficiency of differentiation of hematopoietic precursor cells into erythrocytes/granulocytes while maintaining a low rate of occurrence of cell dysplasia and having the effect of improving the enucleation rate and cell survivability, the present invention can be effectively used for producing erythrocytes/granulocytes in vitro and for treating myelodysplastic syndrome.

8 Claims, 8 Drawing Sheets

METHOD FOR INDUCING HEMOBLAST DIFFERENTIATION

CROSS-REFERENCE TO RELATED APPLICATION AND CLAIM OF PRIORITY

The present invention was made with the support of the Ministry of Health and Welfare of the Republic of Korea, under Project No. A120251, which was conducted in the research project titled "Advanced medical technology development" within the project named "Development of drugs for myelodysplastic syndrome through induction of stem cell differentiation and maturation" by the Industry-Academic Cooperation Foundation, Hanyang University under the management of the Korea Health Industry Development Institute, from Aug. 1, 2012 to Jul. 31, 2014.

Further, the present invention was made with the support of the Ministry of Health and Welfare of the Republic of Korea, under Project No. A101782, which was conducted in the research project titled "Advanced medical technology development" within the project named "Research on efficient differentiation and mechanism of stem cells into erythroid progenitor cells" by the Industry-Academic Cooperation Foundation, Hanyang University under the management of the Korea Health Industry Development Institute, from May 1, 2010 to Mar. 31, 2015.

This application claims priority to and the benefit of Korean Patent Application No. 10-2012-0100821 filed in the Korean Intellectual Property Office on Sep. 12, 2012, the disclosures of which are incorporated herein by reference.

BACKGROUND

Field of the Invention

The present invention relates to a method for inducing hematopoietic cell differentiation and maturation and, more particularly, to an in vitro production of erythrocytes and a treatment of myelodysplastic syndromes using a method for inducing erythrocyte differentiation and maturation.

Background of Technique

The increased demands on medical care from the rapid aging of the population and the development of scientific technology cause an increased use of erythrocytes for transfusion, resulting in a great shortage of erythrocytes. In addition, outbreaks of diseases, such as mad cow disease, swine flu, and malaria significantly reduced people allowing blood donation. Hence, the lack of blood required for transfusions domestically and world widely is causing a setback for patient surgery and treatment. However, this lack of blood will get more serious in the future, and thus it is expected that 55.5% of the domestic blood required will be insufficient (Korea Institute for Health and Social Affairs, 2005). Moreover, transfusion-transmitted infection that may occur due to transfusion causes serious problems in donors, and although founding the problems in advance is hugely expensive, the infection cannot be completely detected (Timmins, N. E.; Nielsen, N. K. Manufactured RBC—Rivers of blood, or an oasis in the desert? Biotechnology Advances 29(6):661-6(2011)). These factors have increased the need for the development of stable erythrocytes that are artificially produced (Olsson, M. L.; Clausen, H. Modifying the red cell surface: towards an ABO-universal blood supply. Br. J. Haematol. 140:3-12; 2008).

Figure 1:
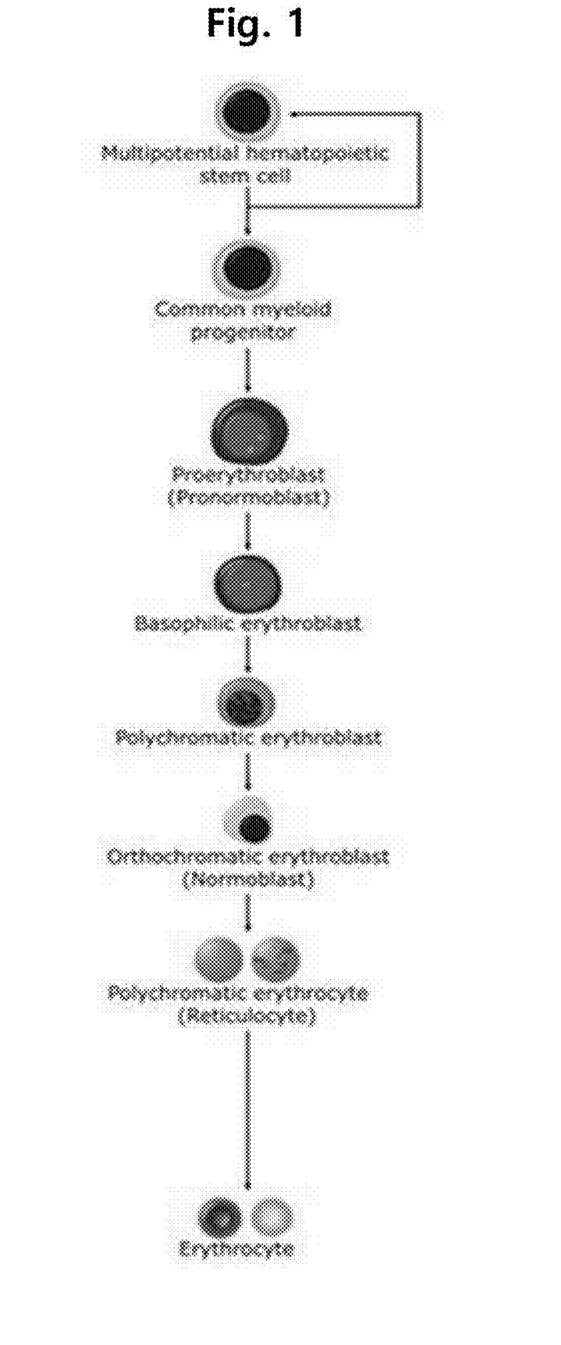
FIG. 1 shows diagram illustrating the erythrogenic process.

FIG. 1 is a diagram illustrating the erythrogenic process. Referring to FIG. 1, the erythroblast matures into a basophilic erythroblast, a polychromatic erythroblast, an orthochromatic erythroblast, and then a reticulocyte. For forming the reticulocyte lastly, an enucleation procedure for efflux of the cell nucleus is needed, and involves the remodeling of the plasma membrane and cytoskeleton. Cytoskeletal proteins, such as spectrin, microtubules, vimentin, and actin filament (F-actin), are involved in this procedure. In addition, the actin filament binds with various proteins (protein 4.1, protein 4.9, spectrin, adducing, tropomysin, tropomodulin, etc.) to make membrane skeleton junctions, thereby forming a surface of the mature erythrocyte. However, most researches relating to the production of artificial blood derived stem cells have merely focused on the amplification of stem cells and progenitor cells until now, and causes and alternatives for the slow maturation of mature cells, a low enucleation rate, low cell viability, and myelodysplasia as one of the factors that induce the low enucleation rate and low cell viability, at the latter half which is the most important and hard stage, have not been known, and researches thereof are insufficient. The cell dysplasia is a very important research subject in order to understand diseases that originate in erythropoiesis and hematopoiesis. The cell maturation, enucleation, and the like at the latter half normally occur in in vivo erythropoiesis, and are necessary for being completed into erythrocytes. For the in vitro production of transfusable artificial erythrocytes, it is necessary to reproduce an in vivo mimiced environment in which the above problems are efficiently controlled in normal situations.

Meanwhile, myelodysplastic syndromes are a group of clonal malignant blood diseases characterized by inefficient hematopoiesis due to progressive pancytopenia and abnormal cell differentiation/maturation. This disease often shows the chronic progress over several years and leads to acute leukemia. The myelodysplastic syndrome involves various molecule abnormalities, which appear in various forms, such as changes in cell cycle and apoptosis, DNA methylation, changes in cancer genes, and changes in bone marrow microenvironments. The incidence of myelodysplastic syndrome is higher than that of normal leukemia, but currently has been underestimated. The median age of onset of this disease has been reported to be the age of 70 in western countries, and as the age increases, the frequency of the disease also increases. One of the 2006 researches reported approximately 12,000 new patients each year in the United States. According to the National Health Insurance Corporation statistics, there were 1845 domestic patients, and approximately 600 new patients are found each year.

The best supportive care has been traditionally employed for the treatment of the myelodysplastic syndrome, and chemotherapy and allogeneic hematopoietic stem cell transplantation have been implemented in the high-risk group patients. However, the average time of survival is only 22 months, and when compared with the survival times by risk groups of patients with lung cancer and stomach cancer, the myelodysplastic syndrome is very severe so that the mid-term survival is similar between the two diseases, and the prognosis of the myelodysplastic syndrome is only 0.4 to 5.7 years. Over the past five years, new concepts of targeted therapeutic agents has changed conditions of the disease and improved the viability, and thus are emerging as new therapies substituting for the best supportive care which has been a therapeutic principle until now, and the efforts for combination therapy with various drugs are being continuously made. These efforts lead to the continuous development of therapeutic agents that are effective in the treatment of the myelodysplastic syndrome, but the percent of patients responding to the therapeutic agents does not exceed 40% for even the best therapeutic agent. Therefore, in the future, fundamentally, the therapeutic agents responding to causes of the myelodysplastic syndrome need to be developed in the future and the therapeutic agents through protein stimulation needs to be developed instead of hematopoietic stem cell transplantation that cannot be implemented on most old age patients.

SUMMARY

Technical Problem

Therefore, the present invention has been made in view of the above-mentioned problems, and an aspect of the present invention is to provide a medium composition for inducing hematopoietic cell differentiation and maturation, the composition being capable of lowering the incidence of cell dysplasia, increasing the enucleation rate and cell viability, and promoting hematopoietic cell differentiation; a method for producing erythrocytes in vitro using the same; and a composition for treating myelodysplastic syndromes.

Technical Solution

In accordance with an aspect of the present invention, there is provided a medium composition containing gelsolin as an active ingredient for inducing the differentiation into erythrocytes or granulocytes from hematopoietic progenitor cells.

In accordance with another aspect of the present invention, there is provided a method for producing erythrocytes or granulocytes in vitro, the method including the steps of: obtaining hematopoietic progenitor cells; contacting the obtained hematopoietic progenitor cells with gelsolin; and culturing the hematopoietic progenitor cells contacted with the gelsolin.

In accordance with still another aspect of the present invention, there is provided a pharmaceutical composition containing gelsolin as an active ingredient for treating myelodysplastic syndromes.

In accordance with still another aspect of the present invention, there is provided a method for treating myelodysplastic syndromes, the method including administering to a subject a pharmaceutical composition containing gelsolin as an active ingredient.

Advantageous Effects

The composition of the present invention has effects of improving the efficiency of differentiation of hematopoietic progenitor cells into erythrocytes or granulocytes, lowering the incidence of cell dysplasia, and increasing the enucleation rate and cell viability, and thus can be useful for the in vitro production of erythrocytes/granulocytes and the treatment of myelodysplastic syndromes.

Meanwhile, the effects of the present invention are not limited to the above-mentioned effects, and other effects could be understood from the following descriptions by a person skilled in the art.

BRIEF DESCRIPTION OF THE DRAWINGS

Panel (a) shows microscopic images obtained from the observation of cell maturation by gelsolin in a first control group and first test group with differentiation into only erythrocytes, and panel (b) shows microscopic images obtained from the observation of cell maturation by gelsolin in a second control group and second test group with simultaneous differentiation into both erythrocytes and granulocytes. Here, red asterisks indicate immature erythrocytes, black arrows indicate granulocytes, Dys black arrows indicate cells exhibiting dysplasia, Dead black arrows indicate dead cells, black-edged arrowheads indicate orthochromatic erythroblasts, and black arrowheads indicate erythrocytes under enucleation.

panel (c) shows a graph illustrating enucleation rate measurement results in the first control group, first test group, second control group, and second test group; and panel (d) shows a graph illustrating dysplasia rate measurement results in the first control group, first test group, second control group, and second test group.

DETAILED DESCRIPTION

First, the terms used herein will be explained.

The term "isolated" or "isolation" used herein, when cells, cell lines, cell cultures, or cell populations are mentioned, refers to being substantially isolated from natural origins, such as cells, cell lines, cell cultures, or cell populations, which can be cultured in vitro, and further refers to physical selection of at least one cell from two or more cell populations, wherein the cell may be selected based on cell morphology and/or expression of various markers.

The term "differentiation" used herein refers to the generation of cell types that are more differentiated than original cell types, and this term means the inclusion of all the partially or eventually differentiated and mature cell types.

The term "medium" used herein refers to a known medium that is used when animal cells are cultured, and means the inclusion of all the known media for culturing animal cells or modified media thereof.

In addition, the term "hematopoietic progenitor cells" refers to the collective term for, including hemocytoblasts, all kinds of cells shown during the differentiation into erythrocytes or granulocytes from the hemocytoblasts.

In addition, the term "erythroid progenitor cells" used herein refers to the collective term for all kinds of cells shown during the differentiation into erythrocytes among hematopoietic progenitor cells, and the term "granulocytic progenitor cells" used herein refers to the collective term for all kinds of cells shown during the differentiation into granulocytes among hematopoietic progenitor cells.

Hereinafter, the present invention will be described in detail.

1. Medium Composition for Inducing Differentiation into Erythrocytes or Granulocytes from Hematopoietic Progenitor Cells An aspect of the present invention provides a medium composition containing gelosin as an active ingredient for inducing the differentiation into erythrocytes or granulocytes from hematopoietic progenitor cells The medium composition of the present invention is used for inducing the differentiation and maturation into erythrocytes, granulocytes, and similar kinds of cells, from hematopoietic progenitor cells, and contains gelsolin as an active ingredient.

The medium is used to culture hematopoietic progenitor cells for the induction of differentiation into erythrocytes or granulocytes, and any medium for culturing animal cells that can be widely known to a person skilled in the art may be used without limitation. The medium may be artificially synthesized, and a commercially prepared medium may be used. Examples of the commercially prepared medium may include Dulbecco's Modified Eagle's Medium (DMED), Minimal Essential Medium (MEM), Basal Medium Eagle (BME), RPMI 1640, F-10, F-12, stemline II, α-Minimal essential Medium (α-MEM), Glasgow's Minimal Essential Medium (G-MEM), Isocove's Modified Dulbecco's Medium (IMDM), MEF, mTeSR-1, and the like, and stemline II may be preferably used, but not limited thereto.

The gelsolin induces the differentiation into erythrocytes or granulocytes by stimulating the hematopoietic progenitor cells and, especially, induces and promotes an enucleation procedure that is necessarily involved during the differentiation into erythrocytes or granulocytes.

The content of gelsolin in the medium composition of the present invention is preferably 5 nM to 1 µM, more preferably 150 nM to 500 nM, and still more preferably 200 nM to 400 nM, but not limited thereto. Less than 5 nM gelsolin may not effectively induce the differentiation into erythrocytes or granulocytes, while more than 1 µM gelsolin may have cytotoxicity, causing a problem in cell viability.

The hematopoietic progenitor cells which are differentiated into erythrocytes by the gelsolin are preferably derived from cord blood or bone marrow, and may be at least one selected from the erythroid progenitor cell group consisting of hemocytoblast, proerythroblast, erythroblast, basophilic erythroblast, polychromatic erythroblast, and orthochromatic erythroblast. Of the hematopoietic progenitor cells, the erythroid progenitor cell differentiated into erythrocyte is differentiated from hemocytoblast, which is a CD34 positive cell, and then matures into proerythroblast, erythroblast, basophilic erythroblast, polychromatic erythroblast, orthochromatic erythroblast, and reticulocyte, sequentially. Hence, the medium composition of the present invention can induce the differentiation into erythrocytes from hematopoietic progenitor cells in the respective differentiation steps.

The hematopoietic progenitor cells which are differentiated into granulocytes by the gelsolin are also preferably derived from cord blood or bone marrow, and may be at least one selected from the granulocytic progenitor cell group consisting of myeloblast, promyelocyte, myelocyte, metamyelocyte, band neutrophil, monoblast, and promonocyte. Of the hematopoietic progenitor cells, the granulocytic progenitor cell differentiated into granulocyte is differentiated from hemocytoblast, which is a CD34 positive cell, and then matures into myeloblast, promyelocyte, myelocyte, metamyelocyte, band neutrophil, monoblast, and promonocyte, sequentially. Hence, the medium composition of the present invention can induce the differentiation into granulocytes from hematopoietic progenitor cells in the respective differentiation steps.

Figure 3:
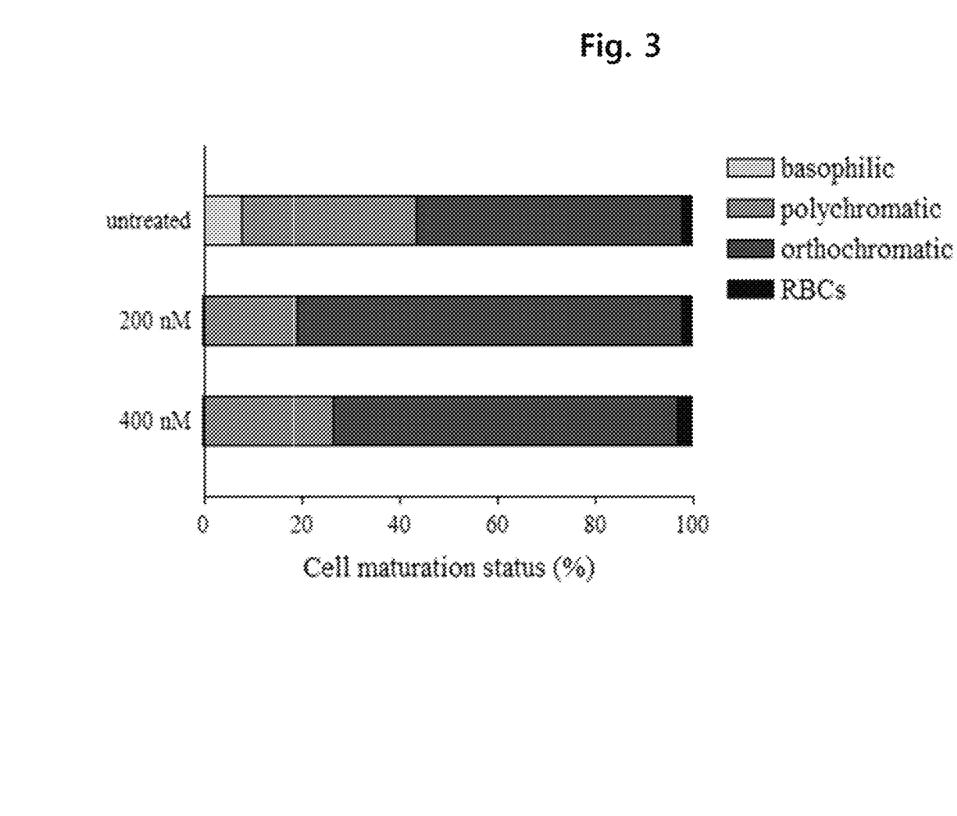
FIG. 3 shows a graph illustrating measurement results of differentiation rate of basophilic erythroblasts treated/untreated with gelsolin.
Figure 4:
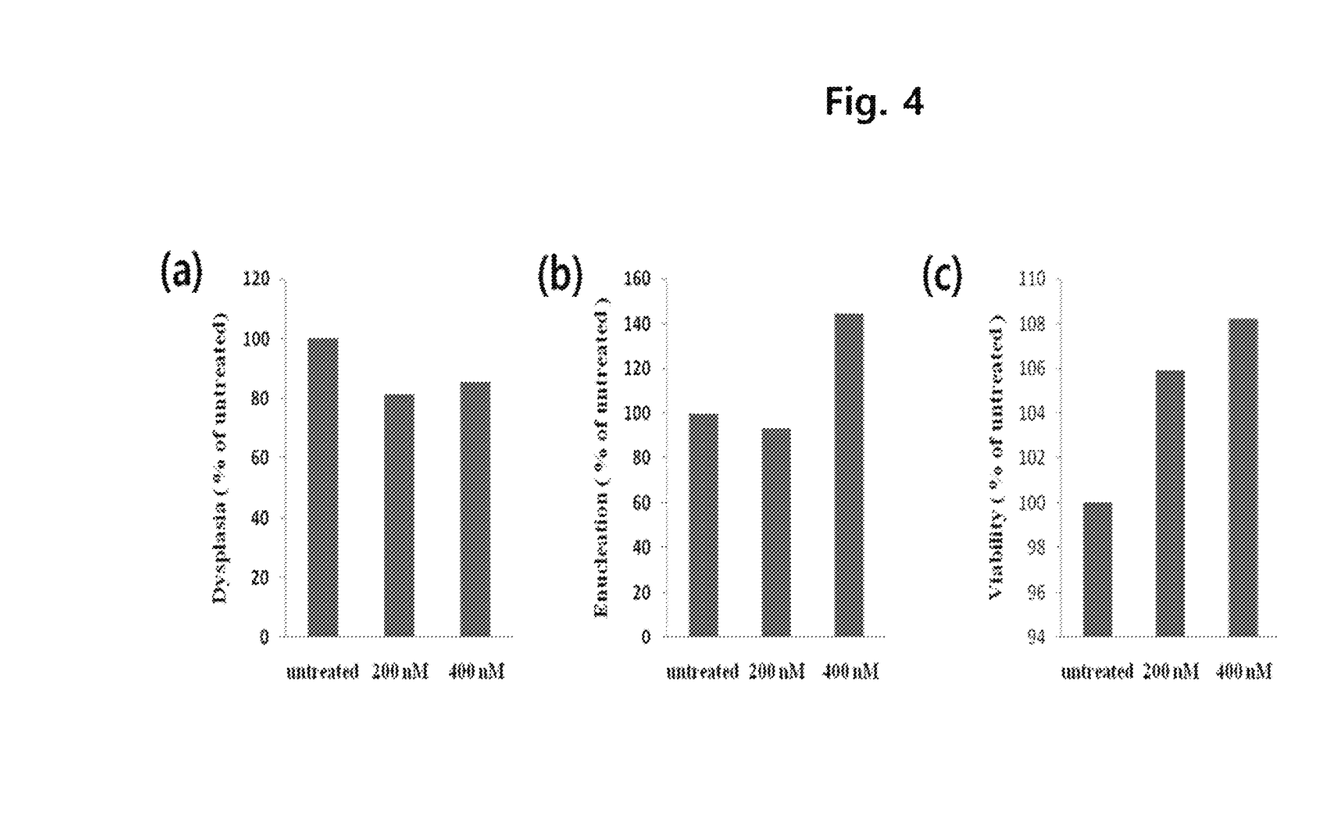
FIG. 4 shows graphs illustrating (a) cell dysplasia rate, (b) enucleation rate, and (c) cell viability of basophilic erythroblasts treated/untreated with gelsolin.

In a specific embodiment of the present invention, by culturing basophilic erythroblasts in a medium containing 200 nM or 400 nM gelsolin, the differentiation into reticulocytes was promoted (see FIGS. 2 and 3), dysplastic cells significantly reduced, and the enucleation rate and cell viability significantly increased (see FIG. 4). In addition, by culturing orthochromatic erythroblasts in a medium containing 400 nM gelsolin, mature erythrocytes were verified to be generated at low cell dysplasia and high differentiation, enucleation, and cell viability (see FIGS. 5 to 7).

2. In Vitro Production of Erythrocytes/Granulocytes

Another aspect of the present invention provides a method for producing erythrocytes or granulocytes from hematopoietic progenitor cells in vitro.

The method for producing erythrocytes or granulocytes, comprises the steps of: 1) obtaining hematopoietic progenitor cells; 2) contacting the hematopoietic progenitor cells, which are obtained in step 1), with gelsolin; and 3) culturing the hematopoietic progenitor cells, which are contacted with the gelsolin in step 2).

The hematopoietic progenitor cells and gelsolin are described as in section "1. Medium composition for inducing differentiation into erythrocytes or granulocytes from hematopoietic progenitor cells". Hence, descriptions of the hematopoietic progenitor cells and gelsolin will be omitted by quoting the descriptions of section "1. Medium composition for inducing differentiation into erythrocytes or granulocytes from hematopoietic progenitor cells", and hereinafter, only distinctive features of the method for producing erythrocytes or granulocytes will be described.

In the obtaining of hematopoietic progenitor cells of step 1), erythroid progenitor cells, such as hemocytoblasts, proerythroblasts, erythroblasts, basophilic erythroblasts, polychromatic erythroblasts, or orthochromatic erythroblasts; and granulocytic progenitor cells, such as myeloblasts, promyelocytes, myelocytes, metamyelocytes, band neutrophils, monoblasts, and promonocytes, are obtained. The hematopoietic progenitor cells are preferably derived from cord blood. In addition, the obtaining of hematopoietic progenitor cells of step 1) may be conducted by various methods known in the art according to the kind of erythroid progenitor cells or granulocytic progenitor cells.

For example, in cases where the hematopoietic progenitor cells to be obtained in step 1) are hemocytoblast, the hematopoietic progenitor cells may be obtained by isolating CD34 positive cells by an immunomagnetic microbead selection method using various known kits that are commercially available (e.g., EasySep CD34 isolation kit).

As another example, in cases where the hematopoietic progenitor cells to be obtained in step 1) are proerythroblasts or erythroblasts, the hematopoietic progenitor cells of step 1) may be obtained by a step of culturing CD34 positive cells in a medium containing hydrocortisone, SCF, IL-3, and EPO. Alternatively, in cases where the hematopoietic progenitor cells to be obtained in step 1) are myeloblasts or promyelocytes, the hematopoietic progenitor cells of step 1) may be obtained by a step of culturing CD34 positive cells in a medium containing SCF, IL-3, EPO, and TPO. The specific concentrations, culturing periods, and the like of active ingredients (hydrocortisone, SCF, IL-3, EPO, and TPO) may be appropriately controlled by a person skilled in the art according to the status of CD34 positive cells and the kind of blood cell to be differentiated. For example, proerythroblasts or erythroblasts, which are erythroid progenitor cells, may be obtained by a step of culturing CD34 positive cells derived from cord blood in a medium containing 8 μM to 12 μM hydrocortisone, 90 ng/ml to 110 ng/ml of SCF, 8 ng/ml to 12 ng/ml of IL-3, and 5 IU/ml to 7 IU/ml of EPO for 6 to 8 days.

As another example, in cases where the hematopoietic progenitor cells to be obtained in step 1) are basophilic erythroblasts, polychromatic erythroblasts, or orthochromatic erythroblasts, the hematopoietic progenitor cells of step 1) may be obtained by step 1') of first culturing erythroblasts in a medium containing SCF, IL-3, and EPO; and step 2') second culturing the first cultured cells in a medium containing SCF and EPO. The specific concentrations, culturing periods, and the like of active ingredients (hydrocortisone, SCF, IL-3, and EPO) may be appropriately controlled by a person skilled in the art according to the status of CD34 positive cells but, preferably, the hematopoietic progenitor cells may be obtained by step 1') of first culturing erythroblasts derived from cord blood in a medium containing 40 ng/ml to 60 ng/ml of SCF, 8 ng/ml to 12 ng/ml of IL-3, and 2 IU/ml to 4 IU/ml of EPO for 5 to 7 days; and step 2') second culturing the first cultured cells in a medium containing 40 ng/ml to 60 ng/ml of SCF, and 1 IU/ml to 3 IU/ml of EPO for 1 to 3 days.

In the contacting of step 2), the hematopoietic progenitor cells obtained in step 1) are stimulated by gelsolin to induce the differentiation and maturation into erythrocytes or granulocytes. The gelsolin may be alone used to treat the hematopoietic progenitor cells, or treat the hematopoietic progenitor cells while contained in the medium for culturing hematopoietic progenitor cells. In cases where the gelsolin is used to treat the hematopoietic progenitor cells while contained in the medium for culturing, the contacting of step 2) and the culturing of step 3) may be simultaneously conducted.

In cases where the gelsolin is used to treat the hematopoietic progenitor cells while being contained in the medium for culturing, the medium contains, preferably 5 nM to 1 μM gelsolin, more preferably 150 nM to 500 nM gelsolin, and still more preferably 200 nM to 400 nM gelsolin. Less than 5 nM of gelsolin may not effectively induce the differentiation into erythrocytes or granulocytes, while more than 1 μM of gelsolin may have cytotoxicity, causing a problem in cell viability.

In the culturing of step 3), the induced differentiation and maturation are allowed to proceed. The differentiation and maturation are preferably allowed to proceed for 18 to 72 hours according to the kind of hematopoietic progenitor cells obtained in step 1). For example, in cases where the hematopoietic progenitor cells obtained in step 1) are basophilic erythroblasts which are one kind of erythroid progenitor cells, the culturing of step 2) is preferably allowed to proceed for 48 hours or longer, while in cases where the hematopoietic progenitor cells obtained in step 1) are polychromatic erythroblasts which are one kind of erythroid progenitor cells, the culturing of step 2) is preferably allowed to proceed for 24 hours or longer. Certainly, in cases where the hematopoietic progenitor cells obtained in step 1) are hemocytoblasts, proerythroblasts, or erythroblasts, the culturing of step 2) is allowed to proceed for a longer time.

The method for producing erythrocytes/granulocytes enables an efficient production of erythrocytes or granulocytes in vitro by improving differentiation ability of the hematopoietic progenitor cells for each step. Especially, the method has an effect of promoting an enucleation procedure that is conventionally unsettled in the in vitro environment, and thus can remarkably increase the production efficiency of erythrocytes or granulocytes in vitro.

Figure 5:
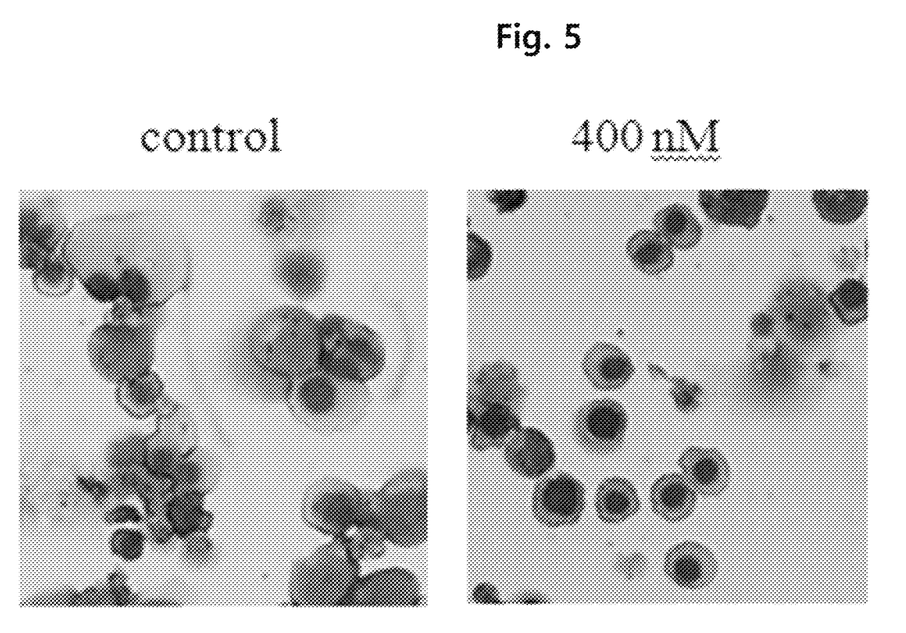
FIG. 5 shows images obtained from morphological observation of polychromatic erythroblasts treated/untreated with gelsolin.
Figure 6:
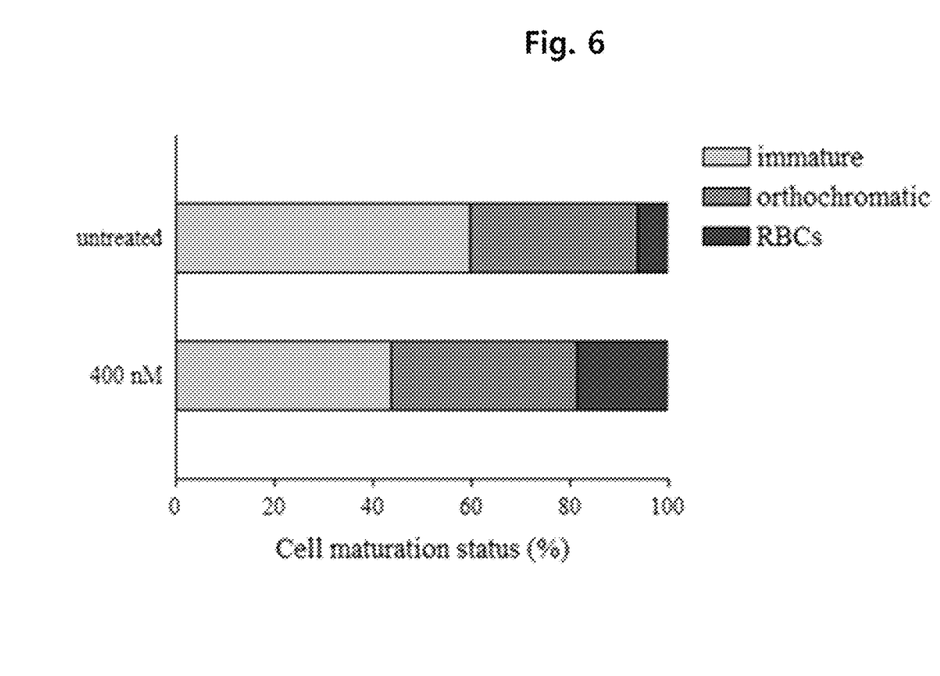
FIG. 6 shows a graph illustrating measurement results of differentiation rate of polychromatic erythroblasts treated/untreated with gelsolin.
Figure 7:
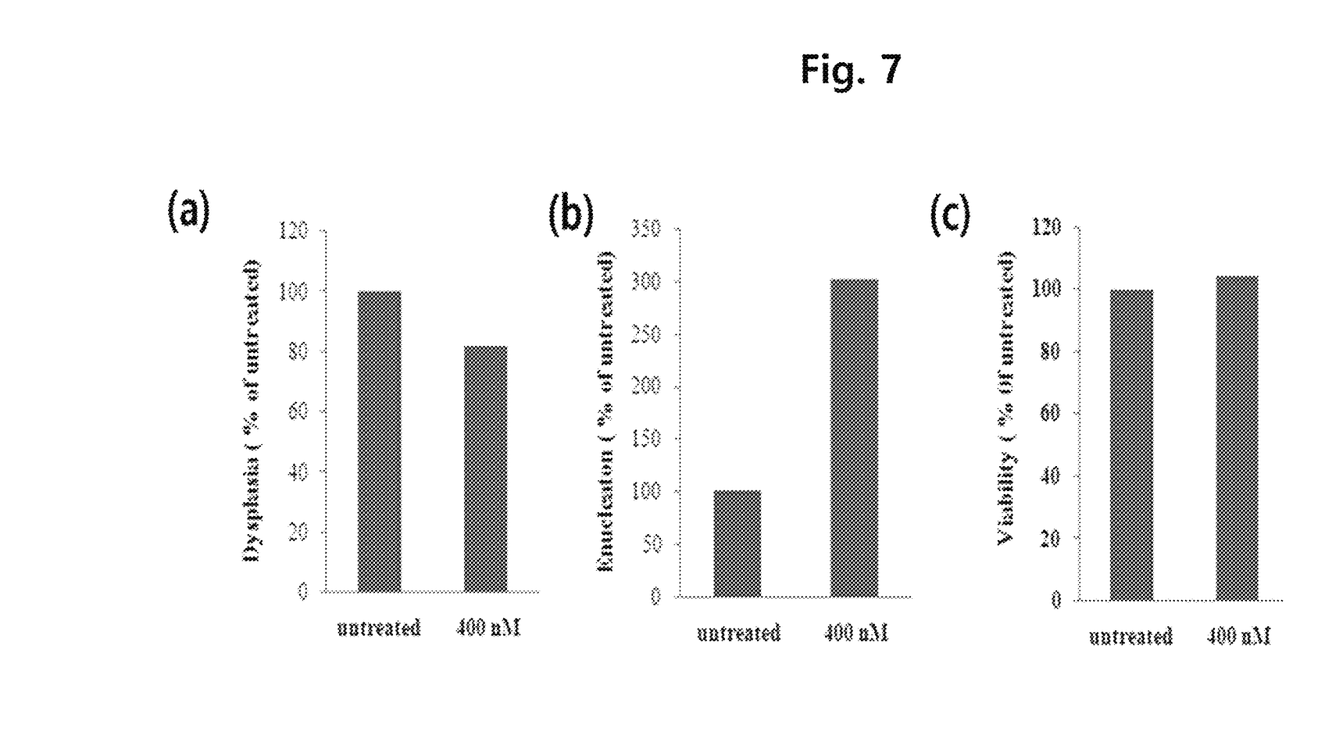
FIG. 7 shows graphs illustrating (a) cell dysplasia rate, (b) enucleation rate, and (c) cell viability of polychromatic erythroblasts treated/untreated with gelsolin.

In a specific example of the present invention, basophilic erythroblasts were cultured in a medium containing 400 nM gelsolin to produce mature erythrocytes with a low dysplasia rate, high differentiation rate, high enucleation rate, and high cell viability (see FIGS. 5 to 7).

3. Composition for Treating Myelodysplastic Syndromes and Method for Treating Myelodysplastic Syndromes Using Same Still another aspect of the present invention provides a pharmaceutical composition containing gelsolin as an active ingredient for treating myelodysplastic syndromes.

Myelodysplastic syndrome (MDS) is a type of disease which is caused by various abnormalities of hemocytoblasts, and refers to a disease in which there are abnormalities in shapes of all kinds of hemocytes including leukocytes, erythrocytes, thrombocytes, and the like, and thus the condition in which the hemocytes are accumulated in the bone marrow but are not sufficient in the peripheral blood. The myelodysplastic syndromes are classified into ① granulocytic series, ② erythroid series, and ③ a megakaryocytic series according to the morphology of the dysplastic cells. The myelodysplastic syndrome may have a risk of developing into myelopoiesis disorder, peripheral cytopenia, and variable acute leukemia, consequently leading to an efficient production of hemocytes. Therefore, in view of the treatment of myelodysplastic syndrome, hematopoietic cell dysplasia inhibitors may stimulate hemocyte differentiation and maturation, and thus can be used to proliferate mature hemocytes subsequently.

The gelsolin, which is one of hematopoietic cell dysplasia inhibitors as described above, induces the production of mature erythrocytes or granulocytes by efficiently controlling low viability according to the maturation of hematopoietic progenitor cells and the cell maturation and increasing the enucleation rate, and thus can be used as an active ingredient of therapeutic agents for diseases, such as myelodysplastic syndromes, especially, erythroid series myelodysplastic syndromes or granulocytic series myelodysplastic syndrome. A specific example of the present invention verified that the gelsolin of the present invention can be used as a therapeutic agent for myelodysplastic syndrome by treating myeloblasts collected from a patient with myelodysplastic syndrome with 400 nM gelsolin to reduce the dysplasia rate and the enucleation rate in erythroid progenitor cells and granulocytic progenitor cells and improve the differentiation rate (see FIG. 8).

In addition to the gelsolin, at least one active ingredient that has similar or the same functions as the gelsolin may be contained. For administration, at least one pharmaceutically acceptable carrier may be further contained. The pharmaceutically acceptable carrier may be at least one selected from a saline solution, sterile water, Ringer's solution, buffered saline, a dextrose solution, a maltodextrin solution, glycerol, ethanol, and a mixture thereof, and if necessary, other common additives, such as an antioxidant, a buffer solution, and a bacteriostatic agent, may be added. In addition, a diluent, a dispersant, a surfactant, a binder, and a lubricant may be additionally added, and formulated into a dosage form for injection such as an aqueous solution, a suspension, or an emulsion, a pill, a capsule, granules or a tablet. Furthermore, the pharmaceutical composition may be preferably formulated according to the disease or ingredient by a suitable method or using a method disclosed in Remington's Pharmaceutical Science (Mack Publishing Company, Easton Pa., 18th, 1990).

The pharmaceutical composition for treating myelodysplastic syndrome of the present invention may be administered in a parental manner (e.g., intravenous, subcutaneous, intraperitoneal, or local) or an oral manner. The dose thereof may be varied according to the weight, age, gender, health condition, diet of a patient, administration time, administration route, excretion rate, severity of disease, and the like.

The daily dose of gelsolin according to the present invention may be 0.01 to 5000 mg/kg, preferably 0.01 to 10 mg/kg, and the ministration of gelsolin may be conducted once or divided into multiple doses a day.

Still another aspect of the present invention is to provide a method for treating myelodysplastic syndrome, the method comprising administering to a subject a pharmaceutical composition containing gelsolin as an active ingredient. Since the method for treating myelodysplastic syndrome of the present invention uses the pharmaceutical composition for treating myelodysplastic syndrome, descriptions of overlapping contents therebetween are omitted to avoid excessive complication of the description of the present specification.

Hereinafter, the present invention will be described in detail with reference to the following examples.

However, the following examples are merely for illustrating the present invention, and thus are not intended to limit the scope of the present invention.

EXAMPLES

Example 1

Preparation of Hematopoietic Progenitor Cells

<1-1> Isolation of CD34 Positive Cells Derived from Cord Blood

After receiving informed consents of cord blood donation from healthy, pregnant women who visited the obstetric department in Hanyang University Seoul Hospital before childbirth, approximately 50 ml to 150 ml of cord blood was collected from the cord immediately after childbirth. CD34 positive cells were isolated from the collected cord blood using EasySep CD34 selection kit (StemCell Technologies, Canada) by the immunomagnetic microbead selection method (Partington et al., J. Immunol. Methods. 1999 Mar. 4; 223(2):195-205).

<1-2> Differentiation and Proliferation into Erythroblasts

The CD34 positive cells ($5 \times 10^4$ cells/ml) isolated in example <1-1> were suspension-cultured in plasma-free and serum-free Stemline (Sigma, U.S.) containing 10 μM hydrocortisone (Sigma, U.S.), 100 ng/ml of stem cell factor (SCF; R&D Systems, U.S.), 10 ng/ml of IL-3 (R&D Systems, U.S.), and 6 IU/ml of erythropoietin (EPO; Calbiochem, U.S.) for 18 days, to be differentiated and proliferated into erythroblasts. The suspension culture was conducted in a $CO_2$ incubator (Sanyo, JAPAN) at 37.

<1-3> Differentiation into Basophilic Erythroblasts

The erythroblasts obtained in example <1-2> were suspension-cultured in plasma-free and serum-free Stemline (Sigma, U.S.) containing 50 ng/ml of stem cell factor (SCF; R&D Systems, U.S.) and 2 IU/ml of erythropoietin (EPO; Calbiochem, U.S.) for 2 days, to be differentiated and proliferated into basophilic erythroblasts which are one kind of erythroid progenitor cells. The suspension culture was conducted in a $CO_2$ incubator (Sanyo, JAPAN) at 37.

<1-4> Differentiation into Polychromatic Erythroblasts

The erythroblasts obtained in example <1-2> were suspension-cultured in plasma-free and serum-free Stemline (Sigma, U.S.) containing 50 ng/ml of stem cell factor (SCF; R&D Systems, U.S.) and 2 IU/ml of erythropoietin (EPO; Calbiochem, U.S.) for 4 days, to be differentiated and proliferated into polychromatic erythroblasts which are one kind of erythroid progenitor cells. The suspension culture was conducted in a $CO_2$ incubator (Sanyo, JAPAN) at 37 while exchanging the medium every two days.

Example 2

Verification of Differentiation Induction Effect of Gelsolin

<2-1> Verification of Induction Effect of Gelsolin on Hematopoietic Progenitor Cell Maturation <2-1-1> Induction of Erythroid Progenitor Cell Maturation The basophilic erythroblasts obtained in example <1-3> were dispensed in a 24-well petri dish at $1 \times 10^6$ cells/ml, and then treated with gelsolin (Adipo Bioscience, U.S.) at concentrations of 0 nM, 200 nM, and 400 nM after 2 hours, followed by culturing for 24 hours. Then, slide smears of the cultured cells were made by a cytospin method using a cell centrifuge (Cellspin, Hanil Science Industrial, KOREA).

<2-1-2> Verification of Induction/Maturation Effect

The smears made in example <2-1-1> were stained with Tripan blue (Sigma-Aldrich, U.S.) to measure cell viability. In addition, the smears were stained with Wright-Giemsa (Sigma-Aldrich, U.S.), and then images of the stained cells were captured by a digital camera (Eclipse TE2000-U, Nikon, JAPAN). The cell morphology was observed, and 400 cells were counted and then the cell maturation status, dysplasia rate, and enucleation rate thereof were measured.

Figure 2:
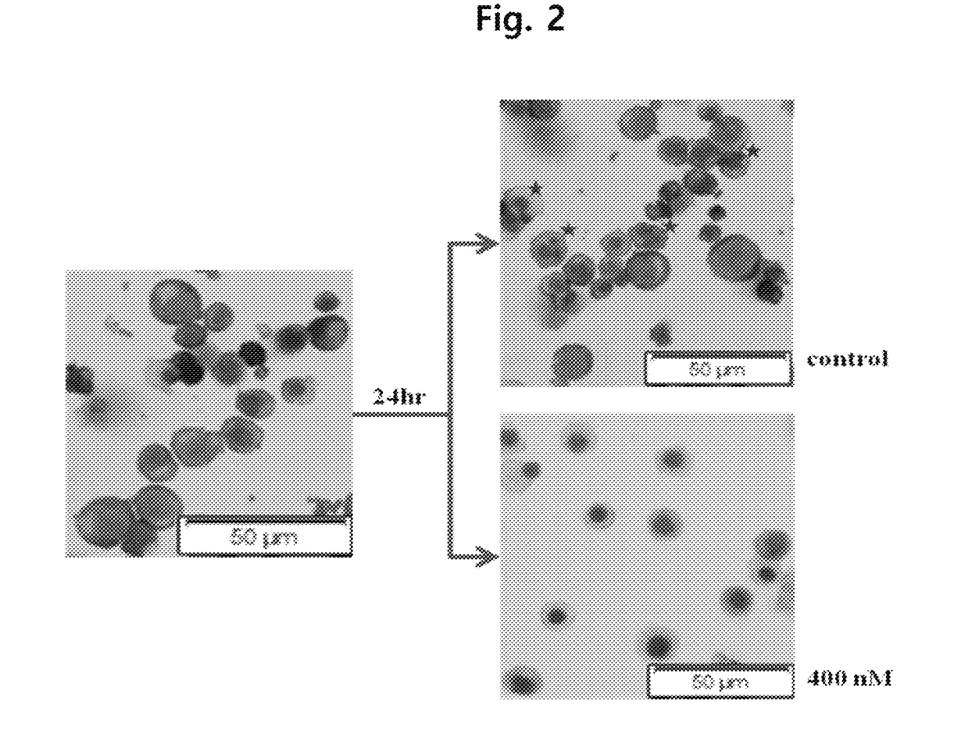
FIG. 2 shows images obtained from morphological observation of basophilic erythroblasts treated/untreated with gelsolin.

First, as a result of cell morphological observation, cells showing cell dysplasia (red asterisks), such as polynucleated cells and cells with fragmented nuclei, were observed in the basophilic erythroblasts untreated with gelsolin, but such cell dysplasia was not observed in the basophilic erythroblasts treated with gelsolin (FIG. 2). In addition, as a result of cell maturation rate measurement, the percent of basophilic erythroblasts and polychromatic erythroblasts was 43.4% in the group untreated with gelsolin, but the basophilic erythroblasts were nearly not observed and the percent of polychromatic erythroblasts were measured to be 19.4% and 26.5% in the groups treated with 200 nM and 400 nM gelsolin, respectively (FIG. 3). Especially, the orthochromatic erythroblasts were increased by 15% or more in the groups treated with gelsolin compared with the group untreated with gelsolin (FIG. 3). It can be seen from the above results that gelsolin promotes the differentiation of basophilic erythroblasts into orthochromatic erythroblasts.

As a result of dysplasia rate measurement, the dysplasia rate was reduced by 19% and 15% in the groups treated with 200 nM and 400 nM gelsolin, respectively, compared with the group untreated with gelsolin ((a) of FIG. 4). The enucleation rate was not increased in the group treated with 200 nM gelsolin, but was increased by 44.5% in the group treated with 400 nM gelsolin, compared with the group untreated with gelsolin ((b) of FIG. 4). Finally, as a result of cell viability measurement, the cell viability was increased by 5% and 8% in the groups treated with 200 nM and 400 nM gelsolin, respectively, compared with the group untreated with gelsolin ((c) of FIG. 4).

It can be seen from the above results that the treatment of basophilic erythroblasts with gelsolin induces the differentiation and maturation of basophilic erythroblasts.

<2-2> Verification of Induction Effect of Gelsolin on Erythrocyte Production

<2-2-1> Induction of Erythrocyte Production

The polychromatic erythroblasts obtained in example <1-4> were dispensed in a 24-well petri dish at 1×106 cells/ml, and then treated with gelsolin (Adipo Bioscience, 미국) at concentrations of 0 nM and 400 nM after 2 hours, followed by culturing for 24 hours. Then, slide smears of the cultured cells were made by a cytospin method using a cell centrifuge (Cellspin, Hanil Science Industrial, KOREA).

<2-2-2> Verification of Induction Effect

The smears made in example <2-2-1> were stained with Tripan blue (Sigma-Aldrich, U.S.) to measure cell viability. In addition, the smears were stained with Wright-Giemsa (Sigma-Aldrich, U.S.), and then images of the stained cells were captured by a digital camera (Eclipse TE2000-U, Nikon, JAPAN). The cell morphology was observed, and 400 cells were counted and then the cell maturation status, dysplasia rate, and enucleation rate thereof were measured.

First, as a result of cell morphology observation, in the polychromatic erythroblasts untreated with gelsolin, most of the polychromatic erythroblasts were left; the percent of differentiated orthochromatic erythroblasts was low; the cell sizes are very large and irregular; and cells showing cell dysplasia through abnormal nucleus division were observed. Whereas, in the polychromatic erythroblasts treated with 400 nM gelsolin, many orthochromatic erythroblasts were observed; the sizes of cells or nucleus are uniform and thus the cells were normally mature; and cell dysplasia was not observed (FIG. 5). For the objective quantification, among the stained and photographed cells, 150 to 200 cell images with respect to the nucleus size and about 400 cell images with respect to the cell size were captured for each test condition. The areas and variations of cells and nuclei were calculated using the image J, and statistically analyzed using the Prism software (Prism, Version 5.0; GraphPad). As for the erythrocytes, the cell area was reduced by about 20% as the cell maturation progressed, and the mean+/−SD of overall cell area was 119.2+/−53.93 and 114.8+/−44.09 (arbitrary units) in the control group and the group treated with gelsolin, respectively. The group treated with gelsolin was verified to show a significantly small size (t-test, p-value<0.0001) and a low standard deviation (SD) thereof, and thus had a more uniform size distribution. The mean+/−SD of cell nucleus area was 115.35+/−80.45 and 92.4+/−42.57 (arbitrary units) in the control group and the group treated with gelsolin, respectively. The group treated with gelsolin was verified to show a significantly small nucleus size (t-test, p-value<0.0001) and a low standard deviation (SD) thereof, and thus also had a more uniform nucleus size distribution.

In addition, as a result of cell maturation status measurement, the percent of polychromatic erythroblasts was 59.7% in the group untreated with gelsolin, but the percent of polychromatic erythroblasts was 43.8% in the group treated with gelsolin (FIG. 6). Especially, the mature erythrocytes were increased by 15% or more in the groups treated with 400 nM gelsolin compared with the group untreated with gelsolin (FIG. 6). It can be seen from the above results that gelsolin promotes the differentiation of polychromatic erythroblasts into erythrocytes.

As a result of dysplasia rate measurement, the dysplasia rate was reduced by 20% in the group treated with 400 nM gelsolin, compared with the group untreated with gelsolin ((a) of FIG. 7). The enucleation rate was increased by three times in the group treated with 400 nM gelsolin, compared with the group untreated with gelsolin ((b) of FIG. 7). Last, as a result of cell viability measurement, the cell viability was increased by 5% in the group treated with 400 nM gelsolin, compared with the group untreated with gelsolin ((c) of FIG. 7).

It can be seen from the above results that the treatment of polychromatic erythroblasts with gelsolin induces the differentiation and maturation of polychromatic erythroblasts.

Example 3

Verification of Treatment Effect on Myelodysplastic Syndrome (MDS)

In addition to <example 2> verifying that gelsolin has an effect of reducing dysplasia occurring during the in vitro differentiation of normal hemocytoblasts, it was verified whether the gelsolin actually has an effect of treating pathologically occurring myelodysplastic syndrome.

<3-1> Verification on in Vitro Treatment Effect on MDS

After receiving informed consents of myeloblast donation from patients diagnosed with refractory cytopenia with multilineage dysplasia (RCMD) by the hemato-oncology department in Hanyang University Seoul Hospital, approximately 3 ml of myeloblasts were collected from bone marrow before treatment.

The collected myeloblasts were suspension-cultured in culture media having the compositions listed in table 1 below for 24 hours, and thus differentiated and proliferated. The suspension culture was conducted in a $CO_2$ incubator (Sanyo, JAPAN) at 37.

TABLE 1

| Culture composition | Differentiation into erythrocytes | | Differentiation into erythrocytes and granulocytes | |
|---|---|---|---|---|
| | First control group | First test group | Second control group | Second test group |
| Hydrocortisone (Sigma, U.S.) | 10 μM | | | |
| SCF (R&D Systems, U.S.) | 100 ng/ml | | | |
| IL-3 (R&D Systems, U.S.) | 10 ng/ml | | | |
| EPO (Calbiochem, U.S.) | 6 IU/ml | | | |
| Thrombopoietin (TPO) (Calbiochem, U.S.) | 0 nM | 0 nM | 100 nM | 100 nM |
| Gelsolin | 0 nM | 400 nM | 0 nM | 400 nM |
| Culture medium | Plasma-free and serum-free Stemline II (Sigma, U.S.) | | | |

The suspension-cultured cells were stained with Wright-Giemsa (Sigma-Aldrich, U.S.), and then images of the stained cells were captured by a digital camera (Eclipse TE2000-U, Nikon, JAPAN). The cell morphology was observed, and 1500 cells were counted and then the cell maturation status, dysplasia rate, and enucleation rate thereof were measured.

First, as a result of cell maturation status comparison between a first control group, which was untreated with TPO to induce only the differentiation into erythrocytes, and a first test group, the percent of mature orthochromatic erythroblasts was 62.5% in the first control group, but 94% in the first test group treated with gelsolin ((a) of FIG. 1). It was verified from the above results that erythroid series cells were cultured with high purity through the treatment with gelsolin.

Next, as a result of cell maturation status comparison between a second control group, which was untreated with EPT and TPO to induce the differentiation into both erythrocytes and granulocytes, and a second test group, 49.2% and 50.8% of cells were differentiated into granulocytic series cells in the second control group and the second test group, respectively. After 48 hours, in the second control group, most of the granulocytic series cells were dead and thus not observed, and only some orthochromatic erythroblasts were observed while showing dysplasia. Whereas, in the second test group treated with gelsolin, even after 48 hours passed, erythroid or granulocytic series cells were continuously observed (47.6%) and normally differentiated mature erythrocytes without immature cells were observed (93.1%) ((b) of FIG. 8).

Figure 8:
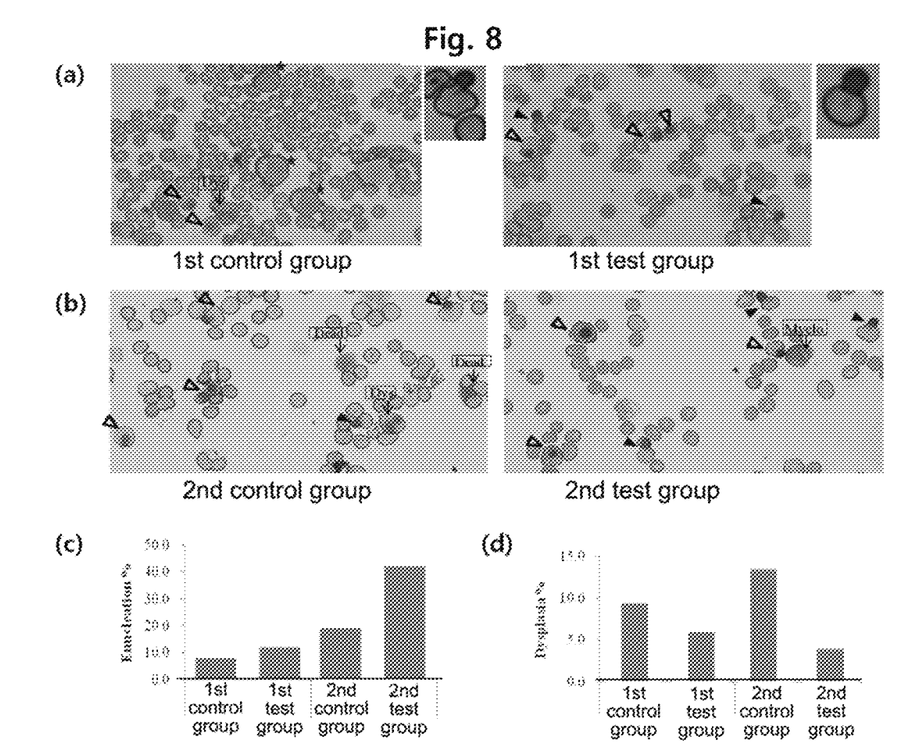
FIG. 8 illustrates verification results of the treatment effect of gelsolin on myelodysplastic syndrome in vitro.

In addition, as a result of enucleation rate analysis, the first and second control groups untreated with gelsolin showed enucleation rates of 7.8% and 18.9%, respectively, but the first and second test groups treated with gelsolin showed enucleation rates of 12% and 42%, respectively, ((c) of FIG. 8). The rate of enucleation rate was improved by approximately two times through the treatment with gelsolin.

Last, as a result of dysplasia rate analysis, the first and second control groups untreated with gelsolin showed dysplasia rate of 9.4% and 13.5%, respectively, but the first and second test groups treated with gelsolin showed dysplasia rate of 6% and 4%, respectively ((d) of FIG. 8).

It can be seen from the above results that gelsolin reduces or alleviates dysplasia of abnormal myeloblasts by promoting differentiation and enucleation of myeloblasts derived from the patient with myelodysplastic syndrome. Accordingly, the gelsolin of the present invention can be used as a therapeutic agent for myelodysplastic syndrome.

As described above, preferable embodiments of the present invention has been exemplified, but the scope of the present invention is not limited to the above particular embodiments, and thus appropriate variations and modifications are possible within the range of claims of the present invention by any person skilled in the art.

The invention claimed is:

1. A method for producing erythrocytes or granulocytes in vitro, comprising:
   (a) obtaining hematopoietic progenitor cells;
   (b) contacting the obtained hematopoietic progenitor cells with gelsolin; and
   (c) culturing the hematopoietic progenitor cells contacted with the gelsolin.

2. The method of claim 1, wherein the hematopoietic progenitor cell is at least one selected from the erythroid progenitor cell group consisting of hemocytoblast, proerythroblast, erythroblast, basophilic erythroblast, polychromatic erythroblast, and orthochromatic erythroblast.

3. The method of claim 2, wherein the hematopoietic progenitor cell is derived from cord blood or bone marrow.

4. The method of claim 1, wherein the hematopoietic progenitor cell is at least one selected from the granulocytic progenitor cell group consisting of myeloblast, promyelocyte, myelocyte, metamyelocyte, band neutrophil, monoblast, and promonocyte.

5. The method of claim 2, wherein the hematopoietic progenitor cell is basophilic erythroblast, polychromatic erythroblast, or orthochromatic erythroblast, and the basophilic erythroblast, polychromatic erythroblast, or orthochromatic erythroblast is obtained by the following sub-steps of:
   (a-1) first culturing erythroblasts in a medium containing SCF, IL-3, and EPO; and
   (a-2) second culturing the first cultured cells in a medium containing SCF and EPO.

6. The method of claim 5, wherein the proerythroblast or erythroblasts are obtained by culturing hemocytoblasts derived from cord blood in a medium containing hydrocortisone, SCF, IL-3, and EPO.

7. A method for treating myelodysplastic syndromes, the method comprising administering to a subject a pharmaceutical composition containing gelsolin as an active ingredient.

8. A method of claim 7, wherein myelodysplastic syndromes are erythroid or granulocytic series myelodysplastic syndromes.

* * * * *